United States Patent [19]
Sasaki et al.

[11] Patent Number: 5,180,789
[45] Date of Patent: Jan. 19, 1993

[54] MEDICAL MATERIALS AND PROCESS FOR PREPARING THE SAME

[75] Inventors: Masatomi Sasaki, Shizuoka; Nobuyoshi Kashiwagi, Saitama, both of Japan

[73] Assignee: Terumo Kabushiki Kaisha, Tokyo, Japan

[21] Appl. No.: 425,200

[22] Filed: Nov. 22, 1989

[30] Foreign Application Priority Data

Apr. 9, 1987 [JP] Japan ................................. 62-85742
Apr. 21, 1987 [JP] Japan ................................. 62-96339

[51] Int. Cl.⁵ .......................... C08F 14/18; C08F 8/18; A61K 31/74; A61M 5/36
[52] U.S. Cl. .............................. 525/326.3; 525/54.23; 525/2.86; 424/78.18; 424/78.31; 424/78.37; 424/402; 604/264
[58] Field of Search ................ 525/326.3, 54.23, 326.3, 525/286; 424/78, 81, 78.18, 78.31, 78.37, 400; 604/264

[56] References Cited

U.S. PATENT DOCUMENTS 4,631,188 12/1986 Stoy et al. ........................... 428/81

FOREIGN PATENT DOCUMENTS 135705 7/1984 European Pat. Off. .
0155432 9/1984 Japan .
0003053 8/1984 PCT Int'l Appl. .

*Primary Examiner*—Paul R. Michl
*Assistant Examiner*—Peter Szekely
*Attorney, Agent, or Firm*—Burns, Doane, Swecker & Mathis

[57] ABSTRACT

Medical materials comprising a reaction product of a copolymer comprising an epoxy group-containing hydrophilic polymeric moiety and a florinated side chain-containing hydrophobic polymeric moiety and a macromolecular compound having a large number of hydroxy groups, amino groups and/or carboxyl groups.

The copolymer is preferably composed of 45-55% by weight of the epoxy group-containing hydrophilic polymeric moiety and the rest of the fluorinated side chain-containing hydrophobic polymeric moiety. The copolymer and the macromolecular compound are bound between the above-mentioned epoxy group and the above-mentioned hydroxyl, amino and/or carboxyl groups.

9 Claims, 8 Drawing Sheets

MEDICAL MATERIALS AND PROCESS FOR PREPARING THE SAME

TECHNICAL FIELD

The present invention relates to medical materials and a process for preparing the same. More particularly, the invention is concerned with medical materials comprising a reaction product of a copolymer having epoxy groups and fluorinated side chains and a macromolecular compound having a large number of hydroxyl groups, amino groups and/or carboxyl groups and a process for preparing the same.

The medical materials of the invention are preferably used as a material for a variety of medical devices, particularly for the medical devices that will come in contact with blood such as artificial organs, plasma separators and hemo-filters.

BACKGROUND OF THE ART

Heretofore, many macromolecular materials have been used as medical materials. Cellulosic materials are especially widely employed because of their safety, processability and economic advantages. On the other hand, biocompatibility is a problem in the use of those macromolecular materials. Especially problematic are such common properties of macromolecular materials as coagulating blood or activating immune system when used for the devices that will come in contact with blood. In order to improve blood coagulative activity of macromolecular materials a method in which cellulose is connected with heparin, for example, has been proposed (Japanese Patent Application Laid-Open-to-Public No. 57288/1978). However, the method is not satisfactorily effective, and development of more improved medical materials is desired.

DISCLOSURE OF THE INVENTION

It is an object of the invention to provide medical materials that are superior in biocompatibility.

According to the invention there are provided medical materials and a process for preparing the same as set forth below.

(1) A medical material comprising a reaction product of a copolymer comprising epoxy-group containing hydrophilic polymeric moiety and fluorinated side chain-containing hydrophobic polymeric moiety and a macromolecular compound containing a large number of hydroxyl groups, amino groups and/or carboxyl groups.

(2) A medical material according to item 1 wherein said hydrophilic polymeric moiety comprises 5-90% weight of acrylic esters and 0.01-60% by weight of an acrylic glycidyl ester and said hydrophobic polymeric moiety comprises 10-90% by weight of an acrylic polyfluorinated alkyl ester.

(3) A medical material according to item 1 wherein a polymer comprising 45-55% by weight of the epoxy group-containing hydrophilic polymeric moiety and the rest of the fluorinated side chain-containing hydrophobic polymeric moiety and a macromolecular compound containing a large number of hydroxyl groups, amino groups and/or carboxyl groups are connected between the above-mentioned epoxy groups and the above-mentioned hydroxyl groups, amino groups and/or carboxyl groups characterized in that composition of the above-mentioned hydrophilic polymeric moiety is:

| Methyl methacrylate | 100 parts by weight |
| Butyl methacrylate | 90-110 parts by weight |
| Hydroxyethyl methacrylate | 35-45 parts by weight |
| Glycidyl methacrylate | 10-15 parts by weight. |

(4) A medical material according to item 1 wherein the macromolecular compound containing a large number of hydroxyl groups is a cellulose.

(5) A method for preparing medical materials which comprises reacting a copolymer comprising epoxy group-containing hydrophilic polymeric moiety and fluorinated side chain-containing hydrophobic polymeric moiety and a macromolecular compound containing a large number of hydroxyl groups, amino groups and/or carboxyl groups.

(6) A method for preparing medical materials according to item 5 which comprises forming as the epoxy group-containing hydrophilic polymeric moiety the composition:

| Methyl methacrylate | 100 parts by weight |
| Butyl methacrylate | 90-110 parts by weight |
| Hydroxyethyl methacrylate | 35-45 parts by weight |
| Glycidyl methacrylate | 10-15 parts by weight. | the weight ratio of said hydrophilic polymeric moiety being 45-55% and the rest being a fluorinated side chain-containing hydrophobic polymeric moiety of a copolymer and binding the above-mentioned epoxy group with the functional group of a macromolecular compound containing a large number of hydroxyl groups, amino groups and/or carboxyl groups.

(7) A method for preparing medical materials according to item 5 wherein the copolymer is contacted in liquid phase in the presence of a Lewis acid catalyst or an alkali catalyst with the surface of a base material containing side terminal of functional OH group to react the reactive epoxy terminal of the copolymer with the functional OH side terminal on the surface of the material thereby forming a bond.

(8) A method for preparing medical materials according to item 7 wherein the Lewis acid catalyst is boron trifluoride.

(9) A method for preparing medical materials according to item 7 wherein the alkali catalyst is sodium hydroxide or potassium hydroxide.

(10) A method for preparing medical materials according to any one of items 5 to 9 wherein dioxane, acetone, methyl ethyl ketone, or tetrahydrofuran is used as a solvent.

As described above, the medical materials of the invention comprises a reaction product of the copolymers mentioned above and a macromolecular compound containing a large number of hydroxyl groups, amino groups and/or carboxyl groups, said copolymer comprising epoxy group-containing hydrophilic polymeric moiety and fluorinated side chain-containing hydrophobic polymeric moiety.

It is believed that, for reducing or nullifying blood coagulative activity of macromolecular compounds, binding to them a polymer in which the hydrophilic moiety and the hydrophobic moiety are well balanced is effective. As the epoxy group-containing hydrophilic moiety, vinyl esters, acrylic esters, vinyl glycidyl esters and acrylic glycidyl esters are preferable. As the fluorinated side chain-containing hydrophobic polymeric moiety are preferably mentioned a polyfluorinated alkyl ester of the vinyl esters and a polyfluorinated alkyl ester of the acrylic acid esters.

More preferably, the epoxy group-containing hydrophilic polymeric moiety is acrylic esters and acrylic glycidyl esters, and the fluorinated side chain-containing hydrophobic polymeric moiety is polyfluorinated alkyl esters of the acrylic acid esters.

Preferable as the acrylic esters is methyl, ethyl, propyl, butyl, hydroxymethyl or hydroxyethyl acrylate or methacrylate or the like The preferable polymer has the formula

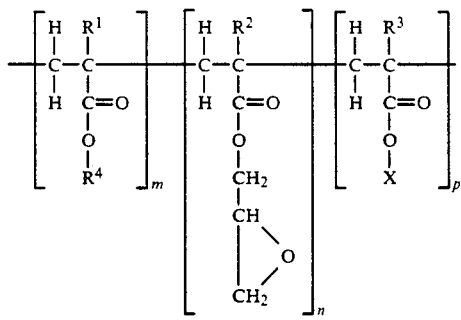

wherein $R^1$, $R^2$ and $R^3$ which may be the same or different are hydrogen atoms or lower alkyl groups, $R^4$ is a hydrogen atom or a lower alkyl group or a hydroxyalkyl group, X denotes a fluorinated alkyl group and m, n and p respectively represent a weight ratio (%) of the starting monomer, m:n:p being 5-90:0.01-60:10-90. The above $R^1$, $R^2$ and $R^3$ are preferably hydrogen or methyl, respectively, and $R^4$ is preferably methyl, ethyl, propyl, butyl, hydroxyethyl or hydroxypropyl. X is preferably a group having the formula $-CF_3$, $-CH_2CF_3$, $-CHF-CF_3$, $-CF_2CF_3$, $-CH_2(CF_2)_2H$, $-CH(CF_3)_2$, $-CH_2(CF_2)_4H$, $-CH_2CH_2C_8H_{17}$ or the like. A weight ratio of the starting monomers in the above-mentioned copolymers is preferably m:n:p=20-50:20-50:20-50.

The especially preferable copolymers have the formula

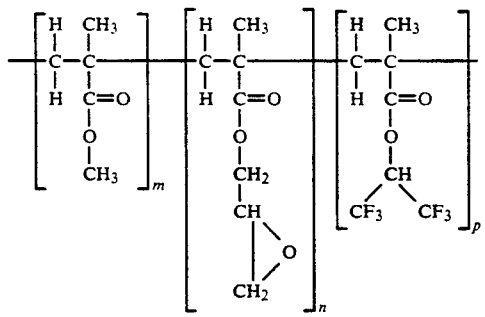

wherein the weight ratio m:n:p is 5-90:0.01-60:10-90.

The weight ratio (%) in terms of the starting monomers of the hydrophilic polymeric moiety to the hydrophobic polymeric moiety is desirably about 70-50:30-50 in the present copolymers. As the starting monomer of the hydrophilic polymeric moiety is preferably used methyl, ethyl, propyl, butyl, hydroxymethyl or hydroxyethyl acrylate or methacrylate or a mixture of them. As the starting monomer of the hydrophobic polymeric moiety is preferably used a polyfluorinated alkyl (for example, trifluoromethyl, 2,2,2-trifluoroethyl, 1,2,2,2-tetrafluoroethyl, pentafluoroethyl, 2,2,3,3-tetrafluoropropyl, di(trifluoromethyl)methyl, 2,2,3,3,4,4,5,5-octafluoroamyl or 2-heptadecylfluorooctylethyl) ester of acrylic or methacrylic acid.

These polymers are prepared by a conventional process such as, for example, aqueous suspension polymerization, block polymerization or solution polymerization.

The epoxy group in the hydrophilic polymeric moiety can be introduced in the polymer either by polymerizing glycidyl acrylate or glycidyl methacrylate together with other monomers or by reacting glycidyl acrylate or glycidyl methacrylate with a hydrophilic polymer in the presence of a polymerization initiator such as, for example, ammonium ceric nitrate or hydrogen peroxide-a ferrous salt. Proportion of the epoxy group in the polymer is suitably 0.01-60% by weight in terms of the amount of glycidyl methacrylate.

On the other hand, cellulose is most preferably employed as the macromolecular compound. In addition, polyvinyl alcohol, ethylene vinyl alcohol polymers, polyacrylic acid or polymethacrylic acid and copolymers of them (for example, ethylene acrylic acid copolymers, polyhydroxyethyl methacrylate chitin, collagen and the like) can be used.

Reaction of the copolymer and the macromolecular compound is carried out by dissolving the copolymer in an appropriate organic solvent such as, for example, acetone, methyl ethyl ketone, dioxane or tetrahydrofuran and adding to the solution a Lewis acid catalyst and a basic catalyst and further a macromolecular compound. The macromolecular compound may be in various formed materials, for example, membrane, hollow fibers and fibers. In this event, the reaction is carried out by dipping the formed material in a solution of the copolymer and a catalyst.

The reaction products thus obtained are biocompatible. Thus, as such properties of the macromolecular compounds as blood-coagulating, immune system-activating and platelet-deforming have become weaker or disappeared, the products are especially suitable for use in artificial organs and medical devices, for example, dialyzers, hemo-filters, plasma separators and residual catheters in the blood vessels which will come in contact with blood.

Examples and test examples will be given below to describe the invention in more detail

EXAMPLE 1

Copolymer Preparation Example 1

In a glass polymerization tube were placed a 0.25 part (by weight, the same hereinbelow) of azobisisobutyronitrile as a polymerization initiator, 12.5 parts of methyl methacrylate, 25 parts of glycidyl methacrylate and 12.5 parts of hexafluoroisopropyl methacrylate. The polymerization tube was cooled in liquid nitrogen, degassed by a vacuum pump, purged with nitrogen, degassed and melt sealed. The tube was heated in a thermostat at 60° C. until the content was solidified. After cooled and opened, the content was taken into tetrahydrofuran. Reprecipitation with methanol yielded a white polymer (referred to as the polymer A). Glycidyl methacrylate content in the polymer was determined to be 44.3% by weight based upon the assay of epoxy group.

Copolymer Preparation Example 2

In a glass polymerization tube were placed a 0.25 part (by weight, the same hereinbelow) of azobisisobutyronitrile as a polymerization initiator, 10 parts of methyl methacrylate, 10 parts of butyl methacrylate, 10 parts of glycidyl methacrylate and 20 parts of hexafluoroisopropyl methacrylate. The polymerization tube was cooled in liquid nitrogen, degassed by a vacuum pump, purged in liquid nitrogen, degassed and then melt sealed. The tube was heated in a thermostat at 60° C. until the content was solidified. After cooled and opened, the content was taken into tetrahydrofuran. Reprecipitation with methanol yielded a white polymer (referred to as the polymer B). Glycidyl methacrylate content in the polymer was determined to be 19.2% by weight based upon the assay of epoxy group.

The polymers A and B prepared as above were respectively dissolved in acetone to prepare 0.5 w/v % solution. To each of the solutions was added boron trifluoride to a concentration of 0.01 w/v %. In 200 ml each of the solutions thus obtained was dipped 0.5 g of a cellulose sheet for a period of 24 hours.

The treated cellulose sheets were thoroughly washed with acetone and water to prepare a medical material of the invention.

Figure 1:
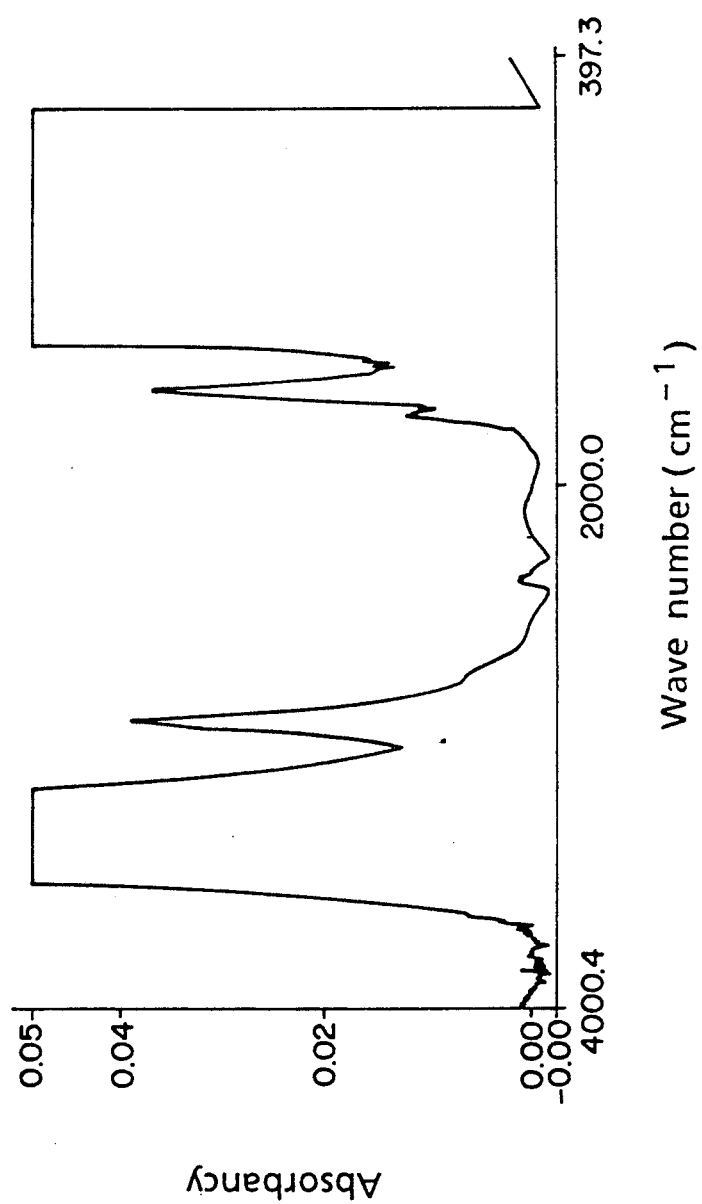
FIG. 1 is a Fourier transform infrared ATR spectrum of the treated cellulose sheet.

Fourier transform infrared ATR spectrum of the material thus obtained is shown in FIG. 1. FIG. 1 is an ATR spectrum of a sample obtained by the treatment of the cellulose with the polymer A, in which an ester carbonyl stretching vibration at 1730 $cm^{-1}$ originated from the polymer A on the surface of the cellulose is detected.

Test for the Determination of Contact Angle

Contact angle with water was measured for the above-prepared medical materials. The measurement was made by the droplet method in which 0.80 μl of distilled water was dropped on the sample, and 60 seconds after the dropping contact angle was measured using a direct-reading goniometer (n=10).

TABLE 1

| Sample | Contact angle (degree) |
| --- | --- |
| Cellulose sheet treated with the polymer A | 61.9 ± 1.2 |
| Cellulose sheet treated with the polymer B | 84.6 ± 1.1 |
| Untreated cellulose sheet | 40.2 ± 1.9 |

It is evident from Table 1 that the surface of the treated cellulose sheet according to the invention was changed to a more water-repellent one than the surface of the untreated cellulose sheet was

EXAMPLE 2

1) In 300 ml each of 0.1, 0.5, 1.0 and 10.0 w/v % aqueous solutions of sodium hydroxide was dipped 0.1 g of a cellulose sheet for 30 min. to convert the hydroxyl group of the cellulose to sodium salt.

2) The sodium-hydroxide treated cellulose sheets were dipped respectively in 0.5 w/v % acetone solution of the polymer B for 24 hours. The treated cellulose sheet was thoroughly washed with water to give a medical material of the invention.

3) Test for contact angle

Contact angle with water was measured for the above-prepared medical materials by the droplet method. Results are shown in Table 2.

TABLE 2

| Sample | Contact angle (degree) |
| --- | --- |
| Cellulose sheet treated with the polymer B (0.1 w/v % aq. sodium hydroxide used) | 38.2 ± 1.5 |
| Cellulose sheet treated with the polymer B (0.5 w/v % aq. sodium hydroxide used) | 86.0 ± 1.8 |
| Cellulose sheet treated with the polymer B (1.0 w/v % aq. sodium hydroxide used) | 84.7 ± 2.1 |
| Cellulose sheet treated with the polymer B (10.0 w/v % aq. sodium hydroxide used) | 79.8 ± 2.4 |
| Untreated cellulose sheet | 43.5 ± 1.8 |

It is seen from Table 2 that in converting the cellulose to the sodium salt the treatment with 0.1 w/v % aqueous solution of sodium hydroxide is insufficient, and a concentration at lowest 0.5 w/v % is required.

EXAMPLE 3

1) The polymer B prepared as above was dissolved respectively in methyl ethyl ketone, acetone, tetrahydrofuran and chloroform to prepare a 0.5 w/v % solution.

2) In the solution of the polymer B prepared under 1) above was dipped 0.1 g of a cellulose sheet for 24 hours, which sheet had been dipped in 300 ml of 0.5 w/v % aqueous solution of sodium hydroxide for 30 min. The treated cellulose sheet was thoroughly washed with water to give a medical material of the invention.

3) Test for contact angle

Contact angle with water was measured for the medical materials prepared as above by the droplet method. Results are shown in Table 3.

TABLE 3

| Sample | Contact angle (degree) |
| --- | --- |
| Cellulose sheet treated with methyl ethyl ketone solution of the polymer B | 87.0 ± 2.1 |
| Cellulose sheet treated with acetone solution of the polymer B | 86.5 ± 1.4 |
| Cellulose sheet treated with tetrahydrofuran solution of the polymer B | 88.2 ± 2.3 |
| Cellulose sheet treated with chloroform solution of the polymer B | 32.8 ± 1.9 |
| Untreated cellulose sheet | 50.0 ± 1.2 |

It is seen from Table 3 that in treating the cellulose sheet with a solution of the polymer B methyl ethyl ketone, acetone or tetrahydrofuran is suitable but chloroform is unsuitable.

TEST EXAMPLE 1

Test For The Ability To Expand Platelets

A test for the ability to expand platelets was carried out for the medical materials of the invention produced in Example 1 which were prepared by treating a cellulose sheet with the polymer B.

In plastic syringes each containing 0.5 ml of 3.8% of aqueous sodium citrate was respectively collected 4.5 ml of venous blood from healthy persons. The blood was transferred into plastic test tubes and centrifuged at 800 r.p.m. for 5 min. The PRP (platelet-rich plasma) was adjusted with a diluent (3.8% aq. sodium citrate: physiological saline solution = 1:9) to a level of platelets of $60,000/mm^3$ to prepare a platelet suspension. The platelet suspension was dropped onto test pieces and allowed for the contact at room temperature for 30 min. The samples were roughly washed with the same diluent as mentioned above, fixed with 2.5% aqueous glutaraldehyde, dried with a series of ethanol and observed under scanning electronic microscope for the attachment to the platelets and morphological changes. Results are shown in Table 4.

The morphological changes were expressed by classification divided into the following three types:

Type I: Transformed into a spheroidal form with three pseudopoda extended from normal disk form;

Type II: With four or more pseudopoda extended and cellular body expanded to half a length of the pseudopodium;

Type III: From thin cellular body extended to half or more of length of the pseudopodium to cellular body fully expanded.

TABLE 4

| Sample | Platelet transformation | | | Number attached |
|---|---|---|---|---|
| | Type I | Type II | Type III | |
| Cellulose sheet treated with the polymer B in THF solution of Example 1 | 71.1 | 27.3 | 1.7 | 241 |
| Cellulose sheet treated with the polymer B in acetone solution of Example 1 | 64.9 | 33.0 | 2.1 | 282 |
| Untreated cellulose sheet | 53.5 | 33.6 | 12.8 | 452 |

It is evident from Table 4 that platelets are transformed with the cellulose sheet of the invention less than with the untreated sheet especially those transformed to the type III being much less. Number of the attached to the sheet is also less with the sheet of the invention than with the untreated sheet.

TEST EXAMPLE 2

Measurement Of Change In The Complement Value

Change in the complement value for the medical materials produced with the polymer B of Example 1 was measured according to the original method of Mayer as described below.

Test sample had in advance been dipped in physiological saline solution to a state of sorption equilibrium. Water on the surface of the sample was roughly removed, and small pieces 20 $cm^2$ in size per piece of the sample were prepared. Each piece was placed in a plastic test tube, to which was then added 1 ml of adult dog serum. After activation by maintaining it at 37° C. for 3 hours change in the complement value $CH_{50}$ was measured. Results are shown in Table 5.

TABLE 5

| Sample | $CH_{50}$ value before contact | $CH_{50}$ value after contact | Proportion of $CH_{50}$ consumed (%) |
|---|---|---|---|
| Cellulose sheet treated with the polymer B in THF solution of Example 1 | 35.2 | 31.5 | 10.5 |
| Cellulose sheet treated with the polymer B in acetone solution of Example 1 | 34.5 | 32.2 | 6.7 |
| Untreated cellulose sheet | 33.8 | 23.4 | 30.8 |

It is evident from Table 5 that decrease in the serum complement value $CH_{50}$ (complement value according to the 50% hemolysis method) is much less with the cellulose sheet of the invention than with the untreated sheet.

EXAMPLE 4

Hollow fibers of cuprammonium regenerated cellulose (ca. 200 μm in inner diameter and ca. 224 μm in outer diameter) were placed in a glass tube, one end of the fiber was connected to a tube which had been connected to an aspirator and the other end was dipped in 0.5 w/v % aqueous solution of NaOH. Then, the inner and outer surfaces of the regenerated cellulose hollow fibers were filled with the NaOH by the use of suction force of the aspirator and allowed to stand for 30 min after the filling. The NaOH on the inner and outer surfaces of the hollow fibers was then discharged. The inner and outer surfaces of the hollow fibers were in turn filled with 0.5 w/v % THF solution of the polymer B of Example 1 in the same manner as above and allowed to stand at room temperature for 24 hours. Then, the solution was discharged followed by washing with an acid, thoroughly with organic solvents (THF, ethanol) and distilled water and drying by warm air blowing at 25° C. In order to secure complete drying the fiber was allowed to stand overnight in an oven at 60° C.

Figure 2:
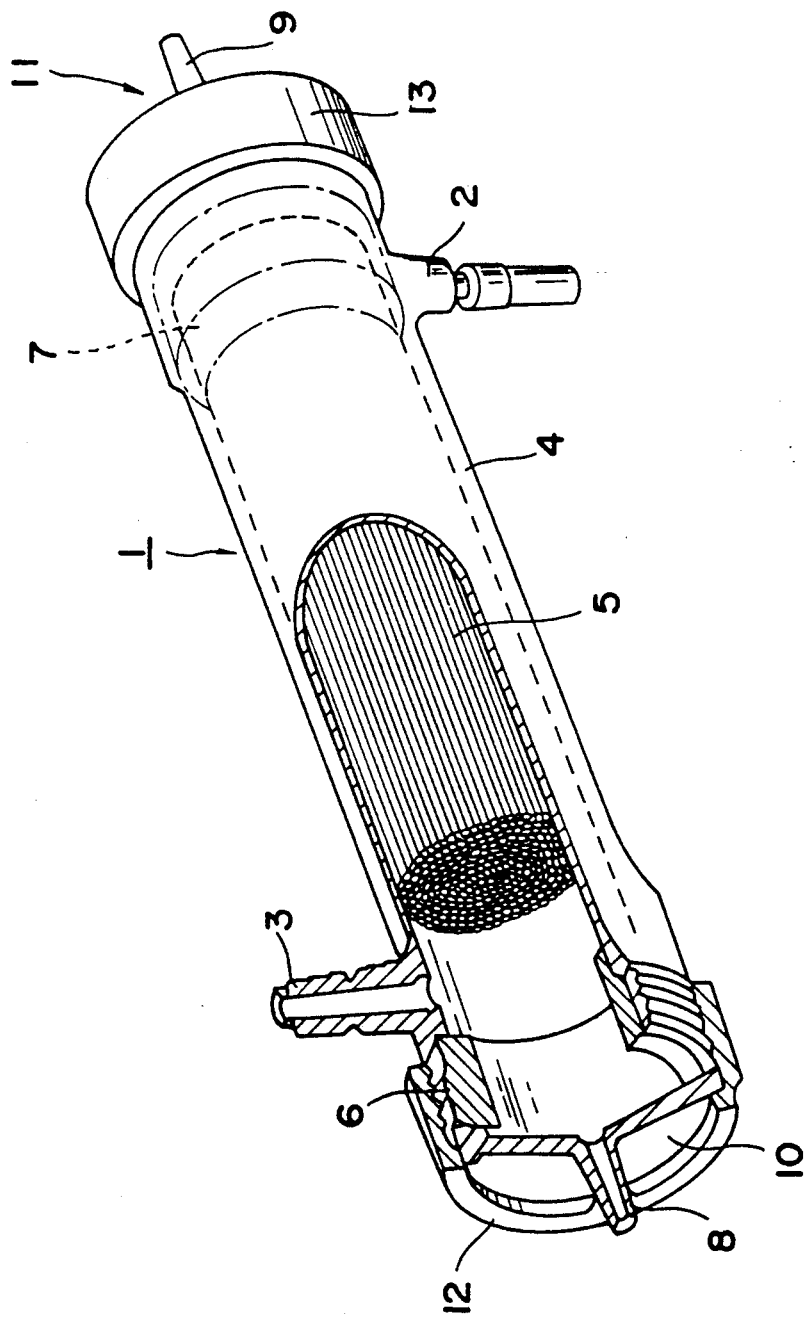
FIG. 2 is a module for extracorporeal circulation with the dialyzer.

The dialyzer (artificial kidney) 1 was prepared as shown in FIG. 2 in which the hollow fiber bundle 5 is formed using 341 hollow fibers of cuprammonium regenerated cellulose 14 cm in effective length and inserted into the cylindrical body 4, both ends of which are then fixed by the urethane potting aids 6, 7 and further equipped with the headers 10, 11, which are firmly attached by the caps 12, 3. Area inside the membrane of the dialyzer was 300 $cm^2$ In addition, there are provided the inlet tube 2 and the outlet tube 3 for the dialyzate near both ends of the cylindrical body 4 of the dialyzer shown in FIG. 2 and also the inflow port 8 and the outflow port 9 for the blood for the headers 10 and 11, respectively. The dialyzer was filled with distilled water, and as it was, was placed in an autoclave and subjected to sterilization treatment at 115° C. for 60 min.

TEST EXAMPLE 3

Test For The Extracorporeal Circulation

Rabbits were fixed on the back on the Kitajima fixing table. Hairs in the operational area were shaved by an electric clippers, and the area was cleaned by an alcoholic cotton ball. Incision along the median line was made with scissors from the submaxillary site through into the clavicle Then, the fascia was opened, and the right (left) carotid artery was detached with care not to injure nerves, ramificated blood vessels and surrounding tissues. Subsequently, the left (right) facial vein was deeply detached with similar care into which was inserted a residual catheter, Surflow (registered trade mark of Terumo K.K.) manufactured by Terumo K.K. equipped with a rubber cap for mixed injection which had been filled with physiological saline solution containing 1 IU/ml of heparin. The catheter was ligated and fixed. Into the above-mentioned artery was inserted a catheter in the same manner as above, which was ligated and fixed.

Figure 3:
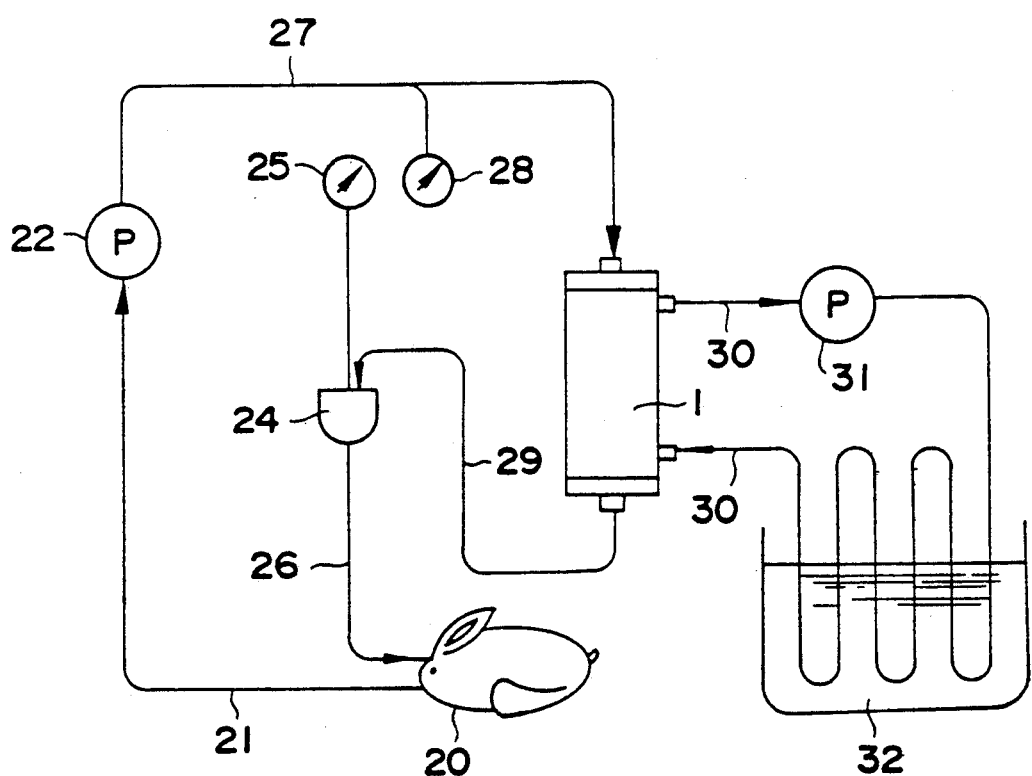
FIG. 3 is an experimental circuit.

An experimental circuit was prepared for the rabbit 20 arranged as above using the dialyzer produced in Example 4 and a membrane dialyzer of untreated cuprammonium regenerated cellulose hollow fibers with the same membrane area as control. Thus, as shown in FIG. 3, the catheter 21 connected to the artery of the rabbit 20 was connected to the pump 22.

Then, the chamber 24 was connected to the vein of the rabbit 20 by means of the catheter 26. The pump 22 and the dialyzer 1 were connected via the tube 27, which was in communication with the "in" 28 of a manometer. The dialyzer 1 was further connected via the tube 29 to the chamber 24 which was in communication with the "out" 25 of a manometer. On the other hand, the inflow and outflow ports for the dialyzate of the dialyzer 1 were connected via the tube 30 which was provided with the pump 31 and was dipped in the water bath 32 at 37° C. The circuit constructed as above was subjected to priming washing with physiological saline solution (100 ml) containing 1 IU/ml of heparin.

Figure 4:
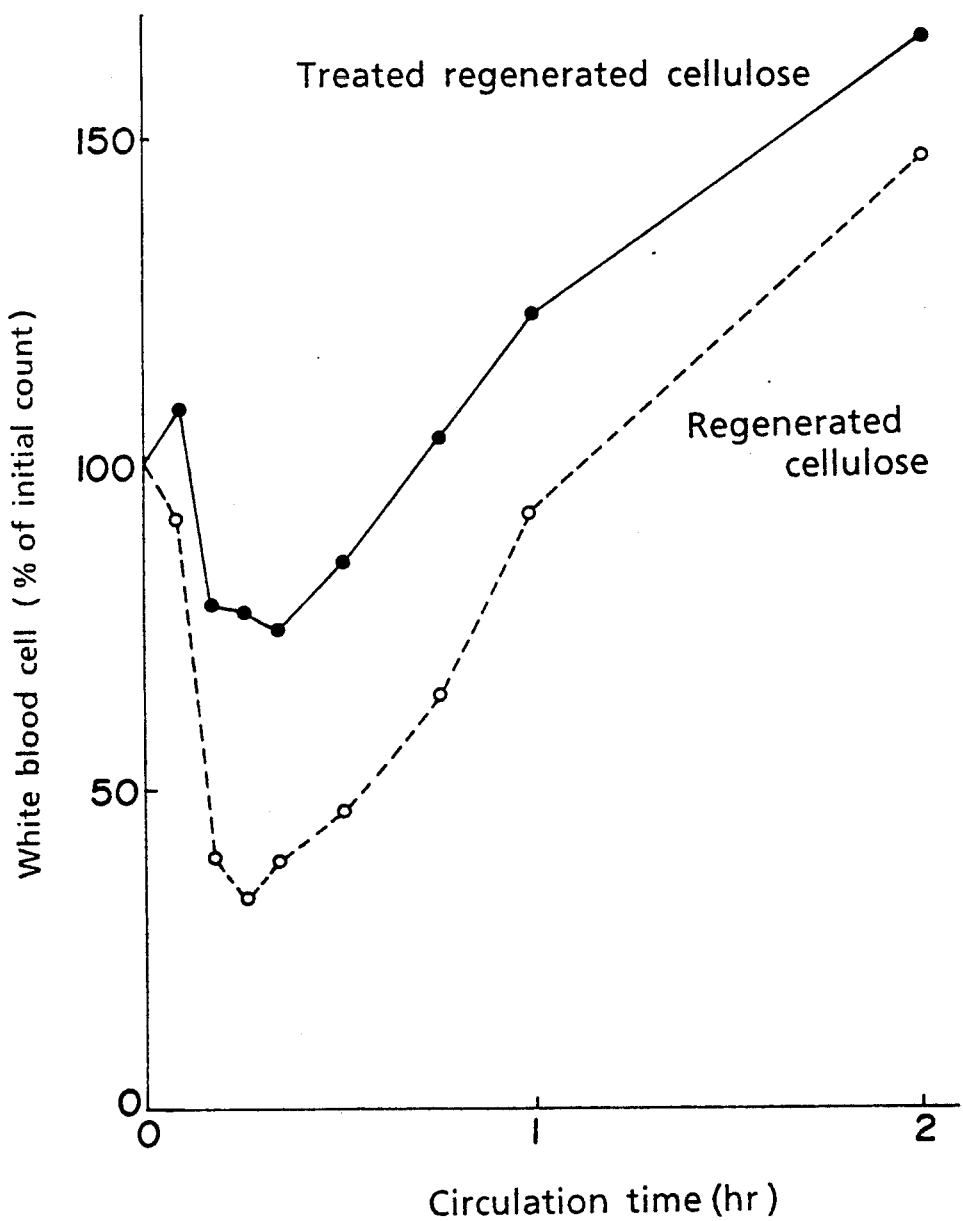
FIG. 4 is a graph indicating change with time of leucocytes.

The extracorporeal circulation was carried out with blood flow set at 10 ml/min. The circulation was started 10 min. after administration of heparin as anticoagulant at a dose of 300 IU/kg. Additional 100 IU/kg of heparin was given 60 min. after start of the circulation. The circulation was continued for a period of 2 hours. Immediately, 5 min., 10 min., 15 min., 20 min., 30 min., 45 min., 60 min. and 120 min. after start of the circulation, respectively, 1 ml of blood was collected and treated with 1.5% EDTA-2Na in physiological saline solution for prevention of coagulation. Blood cells were then counted by means of ELT-8 (manufactured by Orth Instrument Company). Results for the leucocyte count (WBC), platelet count (PLT) and hematocrit value (HCT) are shown in Table 6 and Table 7. Table 6 represents the data obtained from the experimental circuit using the membrane dialyzer produced in Example 4 of cuprammonium regenerated cellulose hollow fibers treated with the polymer B. Table 7 represents the data from the control experimental circuit using the membrane dialyzer of untreated cuprammonium regenerated cellulose hollow fibers. The leucocyte count and the platelet count are $H_t$ corrected ones using the following equation expressed in terms of the $H_t$ value immediately prior to starting the circulation:

$$C_x = C_o \frac{H_{tx}}{H_{to}}$$

wherein $C_x$ is corrected value,
$C_o$ is calculated value on finding,
$H_{tx}$ is corrected base $H_t$ value = initial $H_t$ value, $H_{to}$ is $H_t$ value when the $C_o$ value was obtained.
Variation of the leucocyte count based upon these data is graphically shown in FIG. 4.

TABLE 6

| Time (min) | WBC /mm³* | PIC (%) | PLT ×10⁴/ mm³* | PIC (%) | HCT % | PIC (%) | Δ mmHg |
|---|---|---|---|---|---|---|---|
| Initial | 6100 6100 | 100.00 | 65.90 65.90 | 100.00 | 40.70 | 100.00 | 17 |
| 5 | 5600 6700 | 109.89 | 65.40 78.28 | 118.79 | 34.00 | 83.53 | 56 |
| 10 | 4100 4781 | 78.00 | 56.50 65.88 | 99.98 | 34.90 | 85.74 | 99 |
| 15 | 4000 4705 | 77.13 | 49.20 57.87 | 87.82 | 34.60 | 85.01 | 105 |
| 20 | 3900 4561 | 74.77 | 47.90 56.02 | 85.00 | 34.20 | 85.50 | 119 |
| 30 | 3600 5195 | 85.17 | 88.70 55.85 | 84.75 | 28.20 | 69.28 | 131 |
| 45 | 5400 6407 | 105.04 | 41.50 49.24 | 74.72 | 34.30 | 84.27 | 134 |
| 60 | 6200 7577 | 124.22 | 40.80 49.86 | 75.67 | 33.30 | 81.81 | 179 |
| 120 | 8200 10268 | 168.64 | 43.40 54.35 | 82.47 | 32.50 | 79.85 | 129 |

*Upper line: Measured value
Lower line: Corrected value

TABLE 7

| Time (min) | WBC /mm³* | PIC (%) | PLT ×10⁴/ mm³* | PIC (%) | HCT % | PIC (%) | Δ mmHg |
|---|---|---|---|---|---|---|---|
| Initial | 7000 7000 | 100.00 | 41.10 41.10 | 100.00 | 52.90 | 100.00 | 26 |
| 5 | 4400 6342 | 90.60 | 32.70 47.13 | 114.7 | 36.70 | 69.37 | 30 |
| 10 | 2600 2750 | 39.29 | 34.40 36.39 | 88.55 | 50.00 | 94.51 | 38 |
| 15 | 2200 2309 | 32.98 | 30.50 32.01 | 77.89 | 50.40 | 95.27 | 41 |
| 20 | 2500 2726 | 38.95 | 27.90 80.43 | 74.04 | 48.50 | 91.68 | 52 |
| 30 | 3100 3240 | 46.29 | 27.70 28.95 | 70.46 | 50.60 | 95.65 | 51 |
| 45 | 4300 4522 | 64.60 | 27.10 28.50 | 69.34 | 50.30 | 95.08 | 42 |
| 60 | 6000 6544 | 93.49 | 25.80 28.14 | 68.46 | 48.50 | 91.68 | 50 |
| 120 | 9100 10397 | 148.53 | 24.40 27.87 | 67.33 | 46.30 | 87.52 | 54 |

*Upper line: Measured value
Lower line: Corrected value

REFERENTIAL EXAMPLE

Preparation Of Copolymers

A process according to Japanese Patent Application Laid-Open-to-Public No. 221410/1985 was carried out as follows:

1) Adipic acid and triethylene glycol are subjected to condensation polymerization. The reaction product is peroxidized with hydrogen peroxide to prepare a polymeric peroxide (PPO).

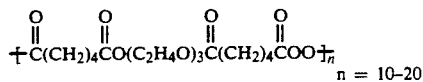

$$n = 10-20$$

2) Acrylic polymers (methyl methacrylate/butyl methacrylate/hydroxyethyl methacrylate/glycidyl methacrylate = (A)40/40/15/5 and (B)40/40/10/10) containing peroxy bonds in the main chain are prepared using the PPO as a polymerization initiator.

3) Block copolymers with a perfluoro acrylate (fluorine-containing monomer) are produced by a dispersion polymerization using the acrylic polymer prepared under 2) above as a polymerization initiator.

4) An aftertreatment of the above-obtained block copolymers is accomplished by heat treatment at 80° C. for 8–10 hours to treat remaining peroxide moiety (in methyl ethyl ketone/methyl isobutyl ketone solution). Furthermore, purification is effected by poor solvent substitution.

EXAMPLE 5

1) The copolymers C and D having a composition as set forth below are respectively dissolved in dioxane to prepare 0.5 w/v % solution.

Copolymer C

A copolymer of fluorine block chain and acrylic block chain (composition ratio of 50:50), said acrylic block chain having a composition of methyl methacrylate: butyl methacrylate: hydroxyethyl methacrylate: glycidyl methacrylate=40:40:15:5 (weight ratio for the starting material [%]).

Copolymer D

A copolymer of fluorine block chain and acrylic block chain (composition ratio of 50:50), said acrylic block chain having a composition of methyl methacrylate: butyl methacrylate: hydroxyethyl methacrylate: glycidyl methacrylate=40:40:10:10 (weight ratio for the starting material [%]).

2) To each of the above solutions was added boron trifluoride to a concentration of 0.01 w/v %. In 200 ml each of the solutions thus obtained was dipped 0.5 g of a cellulose sheet for 24 hours. The treated cellulose sheets were thoroughly washed with water to give a medical material of the invention.

Figure 5:
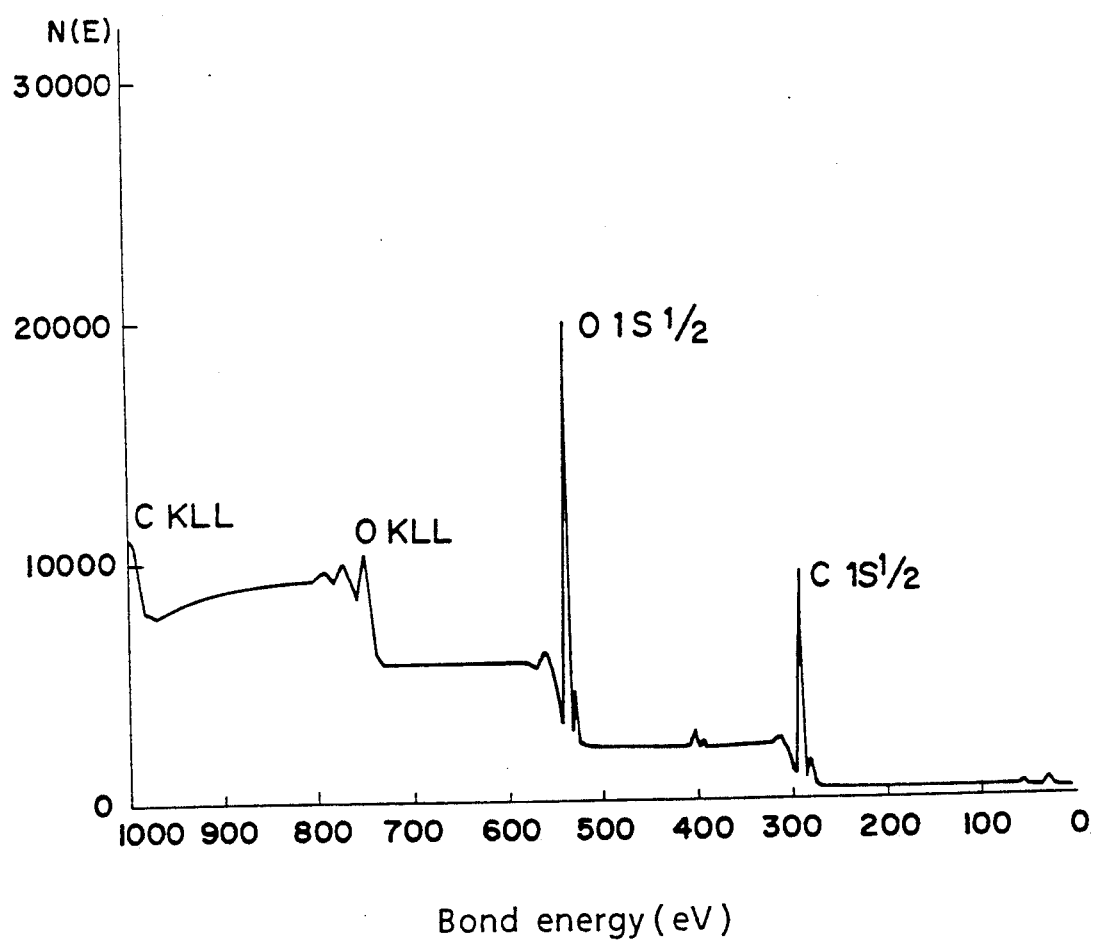
FIG. 5 is an ESCA spectrum of cellulose.
Figure 6:
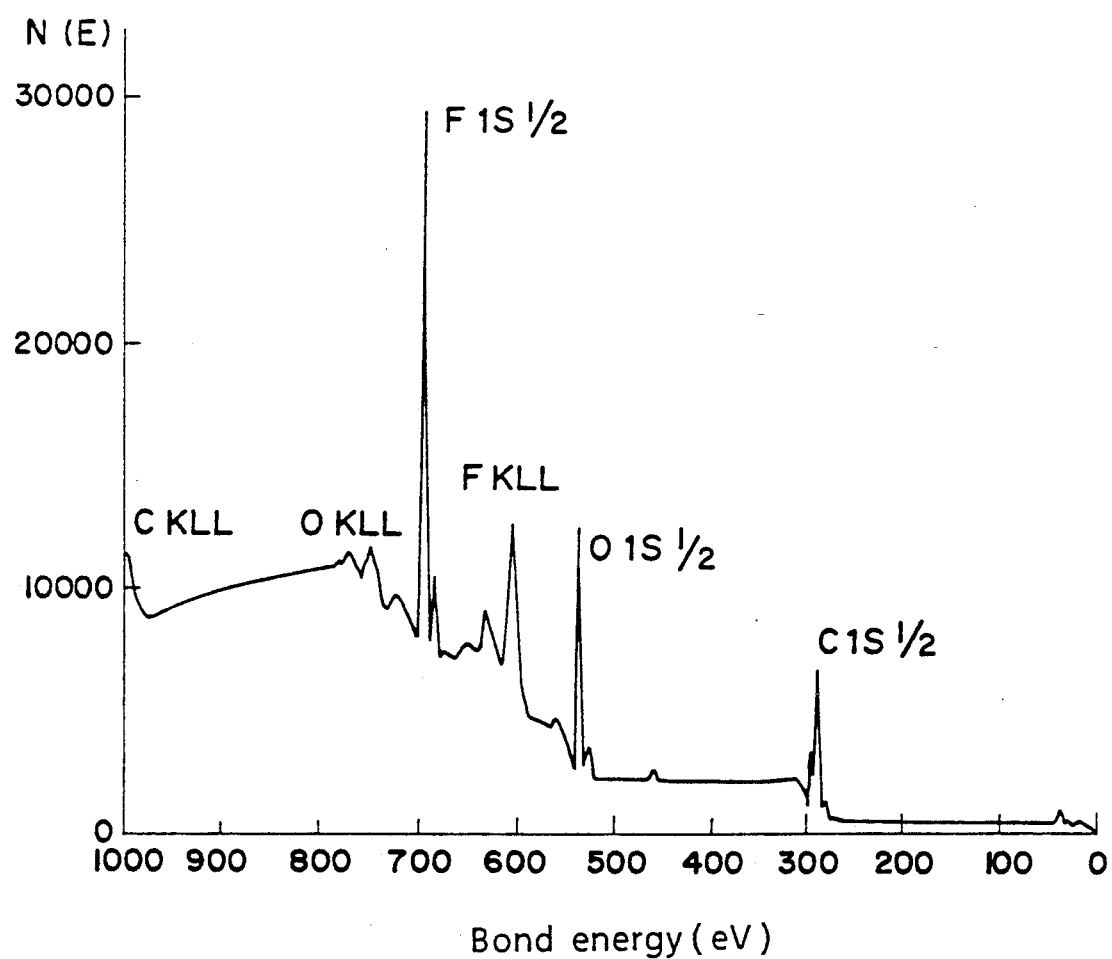
FIG. 6 is an ESCA spectrum of the medical material of the invention.
Figure 7:
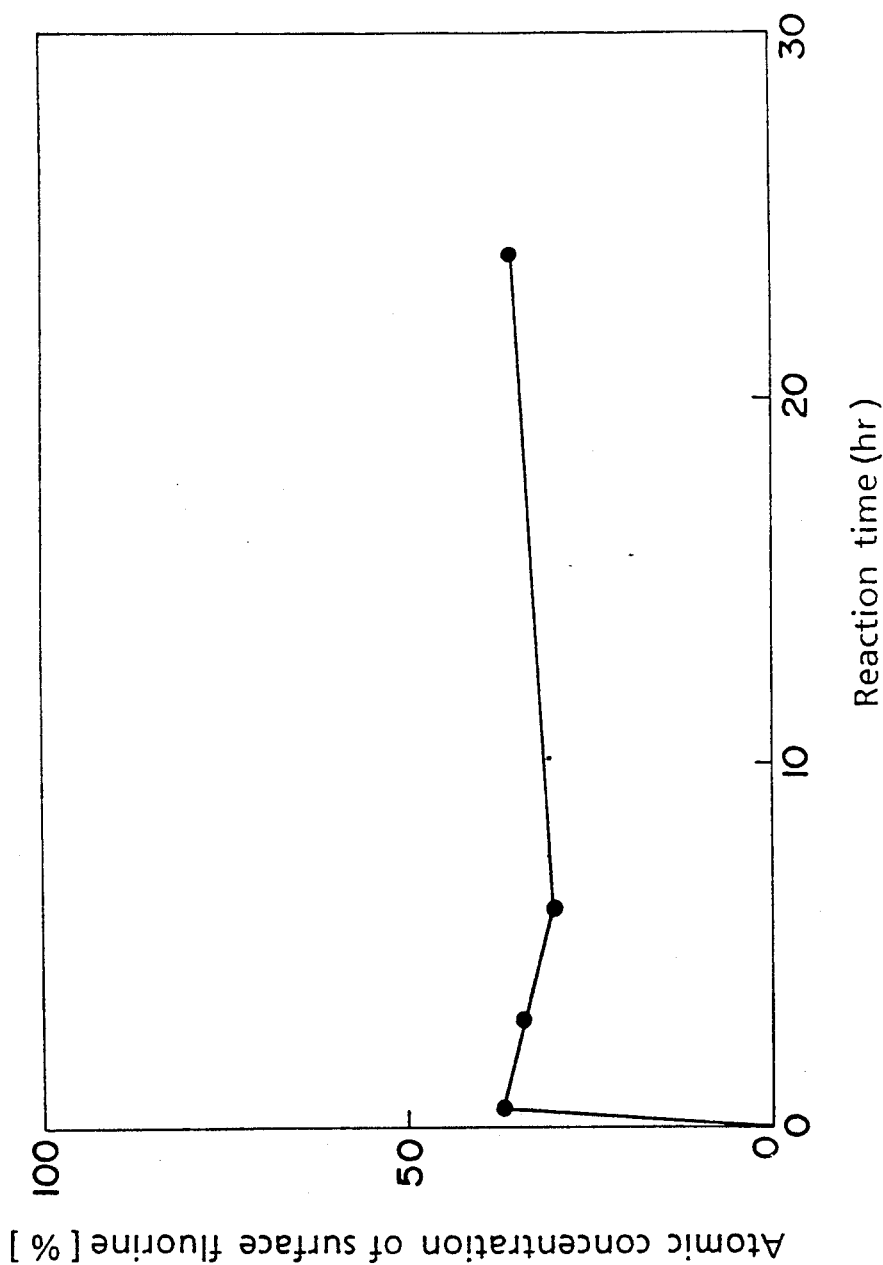
FIG. 7 indicates relationship between the treatment time of cellulose surface and the atomic concentration on cellulose surface.
Figure 8:
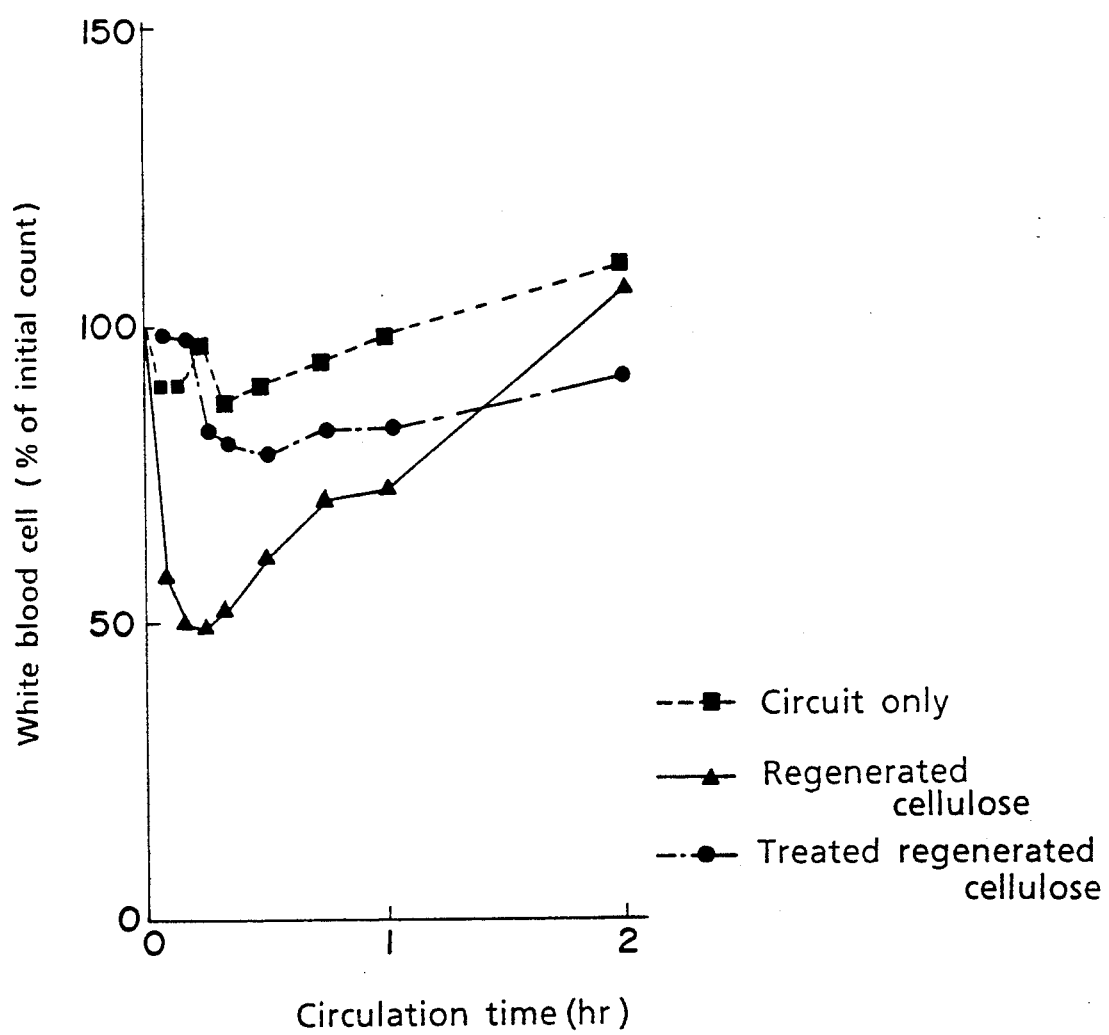
FIG. 8 is a graph indicating change with time of leucocytes.

Electron spectroscopy for chemical analysis (ESCA) spectra of the medical materials thus obtained are shown in FIGS. 5–7. FIG. 5 is an ESCA spectrum of cellulose in which carbon atoms and oxygen atoms are detected on surface of the cellulose. FIG. 6 is an ESCA spectrum of the cellulose treated with the copolymer in which carbon atoms, oxygen atoms and fluorine atoms are detected on the surface of the cellulose. FIG. 7 shows relationship between the treatment time of cellulose surface with the copolymer and the atomic concentration of fluorine on the cellulose surface (as measured by ESCA). Fluorine concentration has reached an almost constant level approximately 30 min. after initiation of the reaction. It is believed that the reaction produces a constant level of the surface composition at an earlier stage.

Test for the Determination of Contact Angle

Contact angle with water was measured for the above-prepared medical materials. The measurement was made by the droplet method in which 0.80 μl of distilled water was dropped on the sample, and 60 seconds after the dropping contact angle was measured using a direct-reading goniometer (n=10).

Results are shown in Table 8.

TABLE 8

| Sample | Contact angle (degree) |
| --- | --- |
| Cellulose sheet treated with the copolymer C | 94.2 ± 1.2 |

TABLE 8-continued

| Sample | Contact angle (degree) |
| --- | --- |
| Cellulose sheet treated with the copolymer D | 94.4 ± 1.4 |
| Untreated cellulose sheet | 49.9 ± 1.2 |

It is evident from Table 8 that the surface of the treated cellulose sheet according to the invention was changed to more water-repellent one than the surface of the untreated cellulose sheet was.

EXAMPLE 6

1) In 300 ml each of 0.1, 0.5, 1.0 and 10.0 w/v % aqueous solutions of sodium hydroxide was dipped 0.1 g of a cellulose sheet for 30 min. to convert the hydroxyl group of the cellulose to sodium salt.

2) The sodium-hydroxide treated cellulose sheets were dipped respectively in 0.5 w/v % dioxane solution of the copolymer D for 24 hours. The treated cellulose sheet was thoroughly washed with water to give a medical material of the invention.

3) Test for contact angle

Contact angle with water was measured for the above-prepared medical materials by the droplet method Results are shown in Table 9.

TABLE 9

| Sample | Contact angle (degree) |
| --- | --- |
| Cellulose sheet treated with the polymer D (0.1 w/v % aq. sodium hydroxide used) | 31.6 ± 2.3 |
| Cellulose sheet treated with the copolymer D (0.5 w/v % aq. sodium hydroxide used) | 95.0 ± 1.7 |
| Cellulose sheet treated with the copolymer D (1.0 w/v % aq. sodium hydroxide used) | 90.7 ± 0.7 |
| Cellulose sheet treated with the copolymer D (10.0 w/v % aq. sodium hydroxide used) | 81.5 ± 2.5 |
| Untreated cellulose sheet | 43.5 ± 1.8 |

It is seen from Table 9 that in converting the cellulose to the sodium salt the treatment with 0.1 w/v % aqueous solution of sodium hydroxide is insufficient, and a concentration at lowest 0.5 w/v % is required.

EXAMPLE 7

1) The copolymer C or D prepared as above was dissolved respectively in methyl ethyl ketone, acetone, and chloroform to prepare a 0.5 w/v % solution.

2) In each of the solutions of the copolymer C or D prepared under 1) above was dipped 0.1 g of a cellulose sheet for 24 hours, which sheet had been dipped in 300 ml of 0.5 w/v % aqueous solution of sodium hydroxide for 30 min. The treated cellulose sheet was thoroughly washed with water to give a medical material of the invention.

3) Test for contact angle

Contact angle with water was measured for the medical materials prepared as above by the droplet method. Results are shown in Table 10.

TABLE 10

| Sample | Contact angle (degree) |
| --- | --- |
| Cellulose sheet treated with methyl ethyl ketone solution of the copolymer D | 99.0 ± 2.3 |
| Cellulose sheet treated with acetone solution of the | 99.7 ± 1.7 |

TABLE 10-continued

| Sample | Contact angle (degree) |
| --- | --- |
| copolymer C | |
| Cellulose sheet treated with chloroform solution of the copolymer C | 32.8 ± 1.9 |
| Untreated cellulose sheet | 50.0 ± 1.2 |

It is seen from Table 10 that in treating the cellulose sheet with a solution of the copolymer C or D methyl ethyl ketone or acetone is suitable, chloroform being unsuitable.

TEST EXAMPLE 4

Test for the Ability To Expand Platelets

Test for the ability to expand platelets was carried out for the medical materials of the invention produced in Examples 5 and 7.

In plastic syringes each containing 0.5 ml of 3.8% aqueous sodium citrate was respectively collected 4.5 ml of venous blood from healthy persons. The blood was transferred into plastic test tubes and centrifuged at 800 r.p.m. for 5 min. The PRP (platelet-rich plasma) was adjusted with a diluent (3.8% aq. sodium citrate: physiological saline solution = 1:9) to a level of platelets of $60,000/mm^3$ to prepare a platelet suspension. The platelet suspension was dropped onto test pieces and allowed for the contact at room temperature for 30 min. The samples were roughly washed with the same diluent as mentioned above, fixed with 2.5% aqueous glutaraldehyde, dried with a series of ethanol and observed under scanning electronic microscope for the attachment to the platelets and morphological changes. Results are shown in Table 11.

The morphological changes were expressed by classification divided into the following three types:

Type I: Transformed into a spheroidal form with three pseudopodia extended from normal disk form;

Type II: With four or more pseudopodia extended and cellular body expanded to half a length of the pseudopodium;

Type III: From thin cellular body extended to half or more of length of the pseudopodium to cellular body fully expanded.

TABLE 11

| Sample | Platelet transformation | | | Number attached |
| --- | --- | --- | --- | --- |
| | Type I | Type II | Type III | |
| Cellulose sheet treated with the copolymer C of Example 5 | 53.6 | 45.6 | 0.8 | 239 |
| Untreated cellulose sheet | 48.8 | 47.7 | 3.5 | 662 |
| Cellulose sheet treated with the copolymer C of Example 3 | 52.5 | 44.1 | 3.3 | 510 |
| Untreated cellulose sheet | 29.1 | 33.1 | 37.3 | 565 |
| | | | | (1000 × 5 views) |

It is evident from Table 11 that platelets are transformed with the cellulose sheet of the invention less than with the untreated sheet especially those transformed to the type III being much less. Number of the attached to the sheet is also less with the sheet of the invention than with the untreated sheet.

TEST EXAMPLE 5

Measurement Of Change In The Complement Value

Change in the complement value for the medical materials produced in Example 5 and Example 7 was measured according to the original method of Mayer as described below.

Test sample had in advance been dipped in physiological saline solution to a state of sorption equilibrium. Water on the surface of the sample was roughly removed, and small pieces 20 $cm^2$ in size per piece of the sample were prepared. Each piece was placed in a plastic test tube, to which was then added 1 ml of adult dog serum. After it was activated by maintaining it at 37° C. for 3 hours change in the complement value $CH_{50}$ was measured. Results are shown in Table 12.

TABLE 12

| | Complement value | | |
| --- | --- | --- | --- |
| Sample | $CH_{50}$ value before contact | $CH_{50}$ value after contact | Proportion of $CH_{50}$ consumed (%) |
| Cellulose sheet treated with the copolymer C of Example 1 | 37.3 | 33.5 | 10.2 |
| Cellulose sheet treated with the copolymer D of Example 7 | 37.8 | 32.8 | 13.2 |
| Untreated cellulose sheet | 39.4 | 25.6 | 35.0 |
| Polymethyl methacrylate sheet | 41.1 | 31.9 | 22.4 |

It is evident from Table 12 that decrease in the serum complement value $CH_{50}$ (complement value according to the 50% hemolysis method) is much less with the cellulose sheet of the invention than with the untreated sheet.

EXAMPLE 8

A dialyzer was prepared in exactly the same way as in Example 4 except that the polymer C or D of Example 5 was used in place of the polymer B of Example 1 therein used.

Test Example 6

Rabbits were fixed on a Kitajima fixing table in exactly the same way as in Test Example 3. A test for the extracorporeal circulation was made using the dialyzer of Example 8 and a membrane dialyzer of untreated cuprammonium regenerated cellulose hollow fibers with the same membrane area as control.

The extracorporeal circulation was carried out with blood flow set at 10 ml/min. The circulation was started 10 min. after administration of heparin as anticoagulant at a dose of 300 IU/kg. Additional 100 IU/kg of heparin was given 60 min. after start of the circulation. The circulation was continued for a period of 2 hours. Immediately, 5 min., 10 min., 15 min., 20 min., 30 min., 45 min., 60 min. and 120 min. after start of the circulation, respectively, 1 ml of blood was collected and treated with 1.5% EDTA-2Na in physiological saline solution for prevention of coagulation. Blood cells were then counted by means of ELT-8 (manufactured by Orth Instrument Company). Results for the leucocyte count (WBC), platelet count (PLT) and hematocrit value (HCT) are shown in Tables 13–15. Table 13 represents the data obtained from the experimental circuit using the membrane dialyzer produced in Example 8 of cuprammonium regenerated cellulose hollow fibers treated with the polymer B. Table 14 represents the data from the control experimental circuit using the membrane dialyzer of untreated cuprammonium regenerated cellulose hollow fibers. Table 15 represents the data from a similar experimental circuit without any dialyzer. The leucocyte count and the platelet count are $H_t$ corrected ones using the following equation expressed in terms of the $H_t$ value immediately prior to starting the circulation:

$$C_x = C_o \frac{H_{tx}}{H_{to}}$$

wherein $C_x$ is corrected value, $C_o$ is calculated value on finding, $H_{tx}$ is corrected base $H_t$ value = initial $H_t$ value, $H_{to}$ is $H_t$ value when the $C_o$ value was obtained.

Variation of the leucocyte count based upon these data is graphically shown in FIG. 10.

TABLE 13

| Time (min) | WBC | | | PLT | | | HCT | |
|---|---|---|---|---|---|---|---|---|
| | DATA (*1) | CAL. (*1) | PIC (%) | DATA (*2) | CAL. (*2) | PIC (%) | DATA (%) | CAL. (%) |
| 0 | 5800 | 5800 | 100 | 36.1 | 36.1 | 100 | 39.9 | 100 |
| 5 | 5600 | 5759 | 99.3 | 36 | 37 | 102.5 | 38.8 | 97.2 |
| 10 | 5500 | 5715 | 98.5 | 34.4 | 35.7 | 98.9 | 38.4 | 96.2 |
| 15 | 4700 | 4808 | 82.9 | 30.8 | 31.5 | 87.3 | 39 | 97.7 |
| 20 | 4500 | 4688 | 80.8 | 31.8 | 33.1 | 91.7 | 38.3 | 96 |
| 30 | 4600 | 4577 | 78.9 | 34.5 | 34.3 | 95 | 40.1 | 100.5 |
| 45 | 4500 | 4814 | 83 | 31.6 | 33.8 | 93.6 | 37.3 | 93.5 |
| 60 | 4500 | 4801 | 82.8 | 31.2 | 33.3 | 92.2 | 37.4 | 93.7 |
| 120 | 5000 | 5334 | 92 | 31.9 | 34 | 94.2 | 37.4 | 93.7 |

*1: mm$^3$
*2: 10$^4$/mm$^3$

TABLE 14

| Time (min) | WBC | | | PLT | | | HCT | |
|---|---|---|---|---|---|---|---|---|
| | DATA (*1) | CAL. (*1) | PIC (%) | DATA (*2) | CAL. (*2) | PIC (%) | DATA (%) | CAL. (%) |
| 0 | 5000 | 5000 | 100 | 37.5 | 37.5 | 100 | 38.1 | 100 |
| 5 | 2900 | 2885 | 57.7 | 34.5 | 34.3 | 91.5 | 38.3 | 100.5 |
| 10 | 2500 | 2507 | 50.1 | 30.4 | 30.5 | 81.3 | 38 | 99.7 |
| 15 | 2400 | 2458 | 49.2 | 29.3 | 30 | 80 | 37.2 | 97.6 |
| 20 | 2600 | 2614 | 52.3 | 28.9 | 29.1 | 77.6 | 37.9 | 99.5 |
| 30 | 3000 | 3064 | 61.3 | 22.1 | 22.6 | 60.3 | 37.3 | 97.9 |
| 45 | 3500 | 3537 | 70.7 | 26.3 | 26.6 | 70.9 | 37.7 | 99 |
| 60 | 3700 | 3643 | 72.9 | 26.1 | 25.7 | 68.5 | 38.7 | 101.6 |
| 120 | 4900 | 5334 | 106.7 | 27.1 | 29.5 | 78.7 | 35 | 91.9 |

*1: mm$^3$
*2: 10$^4$/mm$^3$

TABLE 15

| Time (min) | WBC | | | PLT | | | HCT | |
|---|---|---|---|---|---|---|---|---|
| | DATA (*1) | CAL. (*1) | PIC (%) | DATA (*2) | CAL. (*2) | PIC (%) | DATA (%) | CAL. (%) |
| 0 | 6400 | 6400 | 100 | 37.4 | 37.4 | 100 | 34.2 | 100 |
| 5 | 6000 | 5764 | 90.1 | 39.1 | 37.6 | 100.5 | 35.6 | 104.1 |
| 10 | 6100 | 5779 | 90.3 | 39 | 36.9 | 98.7 | 36.1 | 105.6 |
| 15 | 6500 | 6175 | 96.5 | 43.8 | 41.6 | 111.2 | 36 | 105.3 |
| 20 | 5800 | 5525 | 86.3 | 38.7 | 36.9 | 98.7 | 35.9 | 105 |
| 30 | 6100 | 5779 | 90.3 | 41.6 | 39.4 | 105.3 | 36.1 | 105.6 |
| 45 | 6200 | 6007 | 93.9 | 40.2 | 38.9 | 104 | 35.3 | 103.2 |
| 60 | 6400 | 6272 | 98 | 42.8 | 41.9 | 112 | 34.9 | 102 |
| 120 | 6900 | 7086 | 110.7 | 36.4 | 37.4 | 100 | 33.3 | 97.4 |

*1: mm$^3$
*2: 10$^4$/mm$^3$

INDUSTRIAL APPLICABILITY

The medical materials of the invention which comprises a reaction product of a polymer containing epoxy groups and fluorinated side chains and a macromolecular compound containing a large number of hydroxyl groups, amino groups or carboxyl groups are highly biocompatible and are especially suitable for a material of the medical devices that will come in contact with blood.

Furthermore, the present invention comprises a method for preparing medical materials which comprises reacting the above-mentioned copolymer and the above-mentioned macromolecular compound. According to the invention highly biocompatible medical materials are easily prepared.

What is claimed is:

1. A medical material comprising a reaction product of a copolymer comprising epoxy group-containing hydrophilic polymeric moiety and fluorinated side chain-containing hydrophobic polymeric moiety and a macromolecular cellulosic compound containing a large number of hydroxyl groups, amino groups or carboxyl groups or combination thereof.

2. A medical material according to claim 1 wherein said hydrophilic polymeric moiety comprises 5–90% by weight of acrylic esters and 0.01–60% by weight of an acrylic glycidyl ester and said hydrophobic polymeric moiety comprises 10–90% by weight of an acrylic polyfluorinated alkyl ester.

3. A medical material according to claim 1, wherein a polymer comprising 45–55% by weight of the epoxy group-containing hydrophilic polymeric moiety and the rest of the fluorinated side chain-containing hydrophobic polymeric moiety and a macromolecular cellulosic compound containing a large number of hydroxyl groups, amino groups or carboxyl groups or combination thereof are bound between the above-mentioned epoxy groups and the above-mentioned hydroxyl groups, amino groups or carboxyl groups or combination thereof characterized in that composition of the above-mentioned hydrophilic polymeric moiety is:

| Methyl methacrylate | 100 parts by weight |
|---|---|
| Butyl methacrylate | 90–110 parts by weight |
| Hydroxyethyl methacrylate | 35–45 parts by weight |
| Glycidyl methacrylate | 10–15 parts by weight. |

4. A method for preparing medical materials which comprises reacting a copolymer epoxy group-containing hydrophilic polymeric moiety and the rest of the fluorinated side chain-containing hydrophobic polymeric moiety and fluorinated side chain-containing hydrophobic polymeric moiety and a macromolecular cellulosic compound containing a large number of hydroxyl groups, amino groups or carboxyl groups or combination thereof.

5. A method for preparing medical materials according to claim 4 which comprises forming as the epoxy group-containing hydrophilic polymeric moiety the composition:

| Methyl methacrylate | 100 parts by weight |
|---|---|
| Butyl methacrylate | 90–110 parts by weight |
| Hydroxyethyl methacrylate | 35–45 parts by weight |
| Glycidyl methacrylate | 10–15 parts by weight. | the weight ratio of said hydrophilic polymeric moiety being 45–555 and the rest being a fluorinated side chain-containing hydrophobic polymeric moiety of a copolymer and binding the above-mentioned epoxy group with the functional group of a macromolecular compound containing a large number of hydroxyl groups, amino groups or carboxyl groups or combination thereof.

6. A method for preparing medical materials according to claim 4 wherein the copolymer is contacted in liquid phase in the presence of a Lewis acid catalyst or an alkali catalyst with the surface of a base material containing side terminal of functional OH group to react the reactive epoxy terminal of the copolymer with the functional OH side terminal on the surface of the material thereby forming a bond 7. A method for preparing medical materials according to claim 6 wherein the Lewis acid catalyst is boron trifluoride.

8. A method for preparing medical materials according to claim 6 wherein the alkali catalyst is sodium hydroxide or potassium hydroxide 9. A method for preparing medical materials according to any one of claims 4 to 8 wherein dioxane, acetone, methyl ethyl ketone, or tetrahydrofuran is used as a solvent.

* * * * *

UNITED STATES PATENT AND TRADEMARK OFFICE
CERTIFICATE OF CORRECTION

PATENT NO. : 5,180,789
DATED : January 19, 1993
INVENTOR(S) : Masatomi SASAKI et al It is certified that error appears in the above-identified patent and that said Letters Patent is hereby corrected as shown below:

In Column 17, line 2, delete "555" and insert -- 55% --.

Signed and Sealed this

Twenty-sixth Day of October, 1993

Attest:

BRUCE LEHMAN

*Attesting Officer*       *Commissioner of Patents and Trademarks*

UNITED STATES PATENT AND TRADEMARK OFFICE
CERTIFICATE OF CORRECTION

PATENT NO. : 5,180,789
DATED : January 19, 1993
INVENTOR(S) : Masatomi SASAKI et al It is certified that error appears in the above-identified patent and that said Letters Patent is hereby corrected as shown below:

TITLE PAGE

In Section [22], delete "Filed:   Nov. 22, 1989" and insert

-- [22]   PCT Filed:    April 8, 1988

[86]   PCT No.:      PCT/JP88/00356

§ 371 Date:   November 22, 1989

§ 102(e) Date: November 22, 1989

[87]   PCT Pub. No.: WO88/07872

PCT Pub. Date: October 20, 1988  --

Signed and Sealed this

Twenty-third Day of November, 1993

Attest:

BRUCE LEHMAN

*Attesting Officer*    *Commissioner of Patents and Trademarks*